US006612990B1

(12) United States Patent
Pruter

(10) Patent No.: US 6,612,990 B1
(45) Date of Patent: Sep. 2, 2003

(54) METHOD AND APPARATUS FOR GUIDING NEEDLES

(76) Inventor: Rick L. Pruter, 21 Woodcrest La. NE., Iowa City, IA (US) 52240

( * ) Notice: Subject to any disclaimer, the term of this patent is extended or adjusted under 35 U.S.C. 154(b) by 0 days.

(21) Appl. No.: 09/682,367

(22) Filed: Aug. 24, 2001

Related U.S. Application Data

(63) Continuation-in-part of application No. 09/526,048, filed on Mar. 15, 2000, now Pat. No. 6,296,614, which is a continuation-in-part of application No. 29/103,098, filed on Apr. 8, 1999, now Pat. No. Des. 424,693.

(51) Int. Cl.[7] .................................................. A61B 8/00
(52) U.S. Cl. ....................................... 600/461; 600/462
(58) Field of Search .............................. 600/437, 459, 600/460, 461, 462, 463, 443

(56) References Cited

U.S. PATENT DOCUMENTS

| | | | |
|---|---|---|---|
| 5,235,987 A | | 8/1993 | Wolfe |
| 5,343,865 A | * | 9/1994 | Gardineer et al. .......... 600/461 |
| 5,871,448 A | * | 2/1999 | Ellard ........................ 600/459 |
| 6,139,544 A | * | 10/2000 | Mikus et al. ............... 600/436 |
| 6,311,084 B1 | * | 10/2001 | Cormack et al. .......... 600/411 |

OTHER PUBLICATIONS

Solutions for Ultrasound, CIVCO Medical Instruments Co., Inc., Medical Parkway, 102 Highway 1 South, Kalona, IA 52247 Program for Medical Ultrasound Professionals, Winter 1995, CIVCO Medical Instrument Co., Inc. Medical Parkway, 102 Highway 1 South, Kalona, IA 52247.

* cited by examiner

Primary Examiner—Marvin M. Lateef
Assistant Examiner—Maulin Patel
(74) Attorney, Agent, or Firm—Simmons Perrine Albright & Ellwood, P.L.C.

(57) ABSTRACT

An apparatus and method for guiding a needle in conjunction with a biopsy using a medical imaging device, where an open-ended needle guide with an adjustable slidable multi-gauge needle stop is used to guide a needle during insertion and during a tilting of the needle with respect to the medical imaging device.

20 Claims, 2 Drawing Sheets

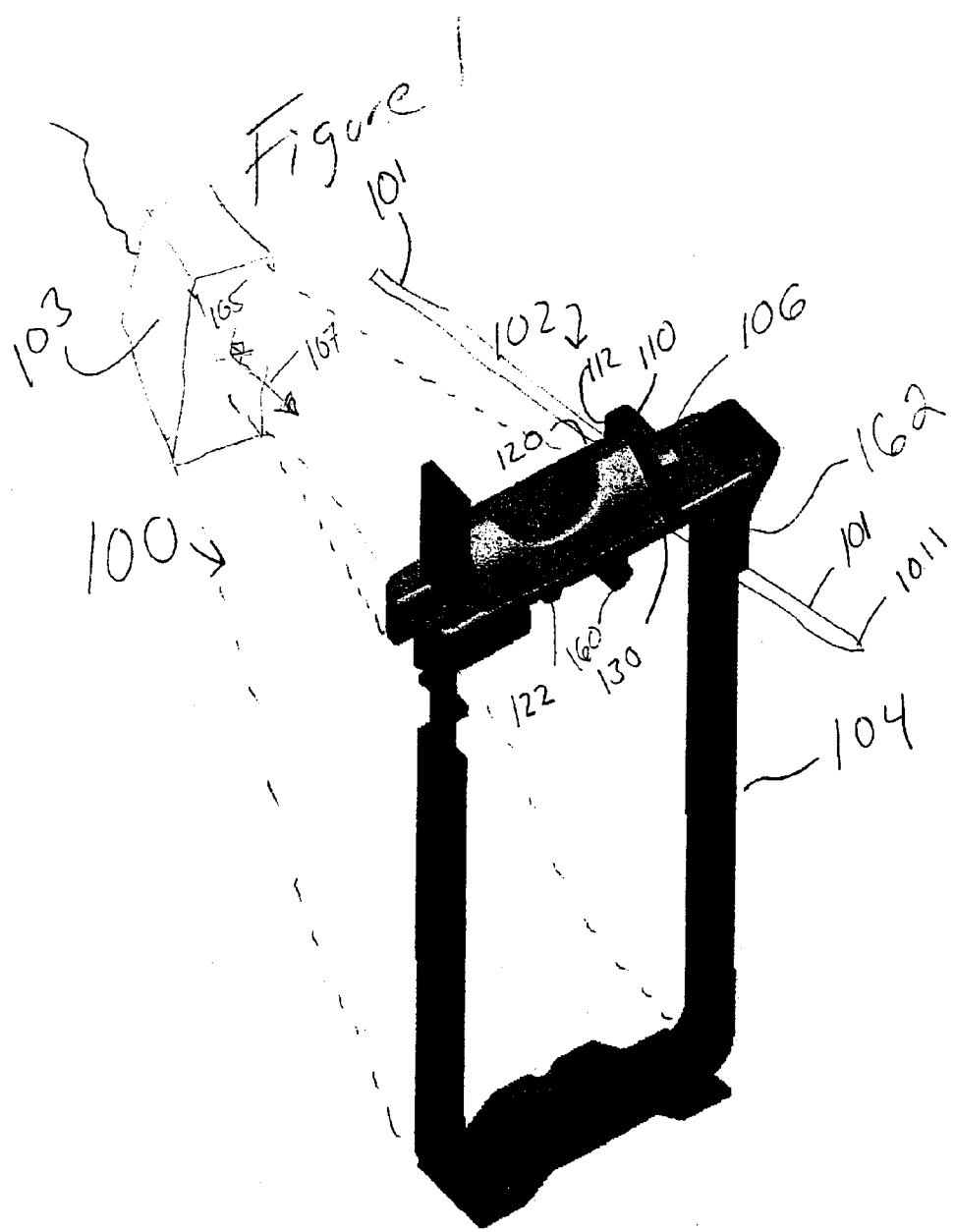

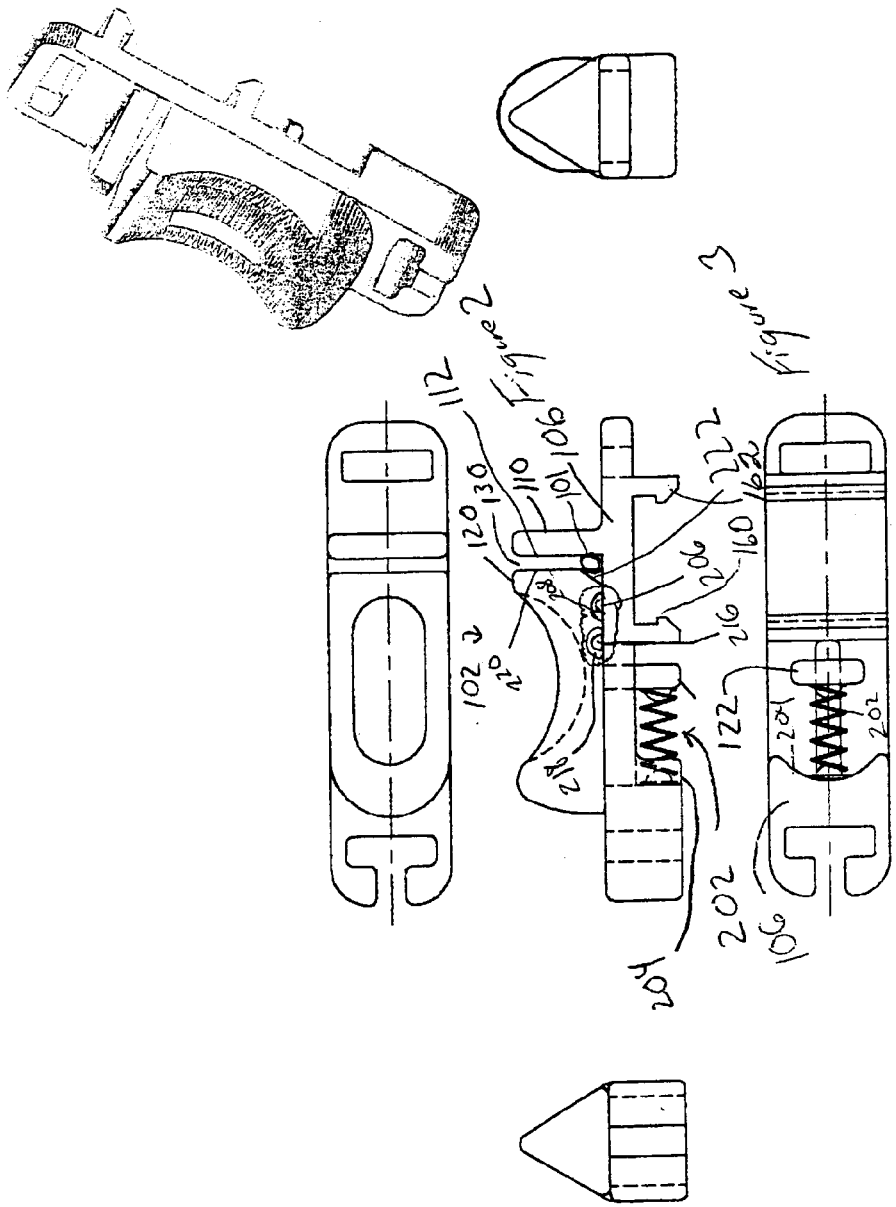

METHOD AND APPARATUS FOR GUIDING NEEDLES

CROSS REFERENCE TO RELATED APPLICATIONS

The present invention is a continuation-in-part application of co-pending application entitled "Needle guide for attachment to ultrasound transducer probe" by the same inventor, the application having Ser. No. 09/526,048 which was filed on Mar. 15, 2000 now U.S. Pat. No. 6,296,614. The above-referenced patent application is itself a continuation-in-part of application Ser. No. 29/103,098, also entitled "Needle guide for attachment to ultrasound transducer probe" filed on Apr. 8, 1999, which has issued as U.S. Pat. No. Des. 424,693. The above-referenced applications and U.S. Design Patent are incorporated herein in their entirety by these references.

BACKGROUND OF INVENTION

In recent years, handheld medical imaging transceivers, such as ultrasound and gamma ray transceivers, have been used extensively for various medical imaging situations. In certain procedures, such as biopsies, it may be desired to tilt a needle with respect to a needle guide or vice versa.

In the past, the physician or medical professional may be required to detach a biopsy needle from a needle guide prior to changing the angle of the needle with respect to the needle guide and transceiver. Other prior art needle guides have included a pair of spaced-apart fixed parallel plates. The medical professional could place the needle between the parallel plates, and it would be free in a plane parallel with the plates, but restricted from large movements outside that plane.

Other prior art needle guides have been used which include a resilient tube coupled to a transducer where the tube has a longitudinal slit through which the needle can be pulled when relative tilting is required.

While these needle guides have been used extensively in the past, they do have some drawbacks. First of all, any model of fixed parallel plate needle guide is limited in the size of needle that can be guided therein. If the needle is too big, it will not fit between the fixed parallel plates. If the plates are too far apart, there is less support being provided in the desired direction. Also, these parallel plate needle guides only provide support in one direction. They provide no support or resistance from motion within the plane of the parallel gap between the fixed plates. This increases the attention required by the medical professional.

Secondly, the resilient slit tube type of needle guide does provide some resistance to motion in the desired plane of motion, but it is limited to only the first portion of that movement or motion. Once the needle is tilted out of the tube, there is no support or resistance to motion in any direction. Additionally, these types of needle guides will work only with specific gauges of needles. They will not work well when a narrow gauge needle is used in a needle guide primarily designed for a larger needle. The narrower needle may fall through the slit. Conversely, a larger needle may not fit in the tube, or it may be difficult to pull through the slit. Consequently, numerous sized slit tube needle guides would be needed to fulfill the needs of a medical professional who uses needles of varying sizes. Additionally, these slit tube type of needle guides may be viewed as unstable in the direction of relative motion. For example, the force required to be applied to the needle to move the needle in the tilted direction decreases as the amount of tilting occurs. To assure that excess tilting does not occur, the medical professional needs to give more attention to the force being applied when the required force decreases with angular displacement.

Consequently, there exists a need for improved methods and apparatus for guiding needles in an efficient manner.

SUMMARY OF INVENTION

It is an object of the present invention to provide an apparatus and method for guiding a tiltable needle in an efficient manner.

It is a feature of the present invention to utilize a multi-gauge adjustable needle guide.

It is another feature of the present invention to include a slidable needle stop.

It is another feature of the present invention to include a slide-ably adjustable needle guide stop with a bias force for closing the needle guide.

It is another feature of the present invention to include needle stops having contours for engaging needles.

It is an advantage of the present invention to achieve improved efficiency in guiding needles.

The present invention is an apparatus and method for guiding needles designed to satisfy the aforementioned needs, provide the previously stated objects, include the above-listed features, and achieve the already articulated advantages. The present invention is carried out in a "physician burden-less" manner in a sense that the burden on a physician or other medical professional in guiding needles during the process of tilting has been greatly reduced.

Accordingly, the present invention is an apparatus and method including a slidable needle stop in a multi-gauge adjustable needle guide.

BRIEF DESCRIPTION OF DRAWINGS

The invention may be more fully understood by reading the following description of the preferred embodiments of the invention, in conjunction with the appended drawings wherein:

FIG. 1 is a partially exploded perspective view of the apparatus of the present invention.

FIG. 2 is an enlarged partially cut-away side view of the needle guide of FIG. 1, where the cut-away portion exposes a plurality of detent mechanisms.

FIG. 3 is a bottom view of the needle guide of FIGS. 1 and 2.

DETAILED DESCRIPTION

Now referring to the drawings wherein like numerals refer to like matter throughout, and more specifically referring to FIG. 1, there is shown a needle guide assembly 100, of the present invention which includes a needle guide 102 with a needle 101 disposed therein. Needle guide 102 is coupled to medical imaging device 103, which could be an ultrasound transducer, gamma ray transceiver or other imaging device, via a medical imaging device retaining strap 104, which could be an elastic strap, such as rubber or a less elastic strap, such as fabric or leather. Cables, wires, rope, brackets, clamps or any other suitable substitute could be used for a medical imaging device retaining strap 104. Needle guide 102 is preferably a plastic material, such as ABS or equivalent; however, other materials, such as aluminum, surgical steel, and any other suitable material could be substituted.

The medical imaging device 103 has a transmitting end 105, which may be a planar face with a vertical axis 107 extending orthogonally therefrom.

The term "vertical axis 107" is used herein to convey that the axis is orthogonal to the transmitting surface end 105. Depending on the orientation of the medical imaging device 103, the vertical axis 107 may be pointed in any direction with respect to the patient or an earth reference. In normal operation, the medical imaging device 103 is often held, at least at first, with the transmitting end 105 in, a substantially horizontal (earth reference) arrangement. This arrangement results in the vertical axis 107 being orientated in a vertical (earth reference) direction.

Needle guide 102 has a slidable needle stop 120 which may be contoured on its top side to facilitate engagement with a human finger or thumb. Slidable needle stop 120 is preferably slidable along needle guide main body 106 which contains a first needle stop 110. However, other arrangements between the slidable needle stop 120 and first needle stop 110 could be substituted. First needle stop 110 may be vertical and have a planar needle engagement surface 112 as shown, but other arrangements could be employed as well.

Also shown in FIG. 1 are members 160 and 162, which can form a pliable clip for attaching needle guide 102 to a bracket (not shown) coupled to a medical imaging transceiver when strap 104 is not used.

Now referring to FIG. 2, there is shown a partially cut-away side view of the needle guide 102 of FIG. 1. Needle guide 102 is shown having a spring 202, which could be a simple metal or plastic spring, or it could be any resilient member or other apparatus capable of biasing sliding spring stop 122 so as to tend to minimize the width of needle gap 130. Spring 202 is shown disposed between fixed spring stop 204 and sliding spring stop 122. Needle guide 102 is also shown in the cut-away portion as having a needle guide main body 106, first detent protrusion 206 and second detent protrusion 216 which are received by first detent protrusion receiving void 208 and second detent protrusion receiving void 218 both found in slidable needle stop 120. Slidable needle stop 120 is shown having a top leading edge 220 and a bottom angled leading edge 222. Preferably, the pressure exerted by spring 202 is sufficient to hold needle 101 stationary unless a force other than gravity acts upon Now referring to FIG. 3, there is shown a bottom view of the needle guide 102 of FIGS. 1 and 2.

In operation, the apparatus and method of the present invention as described and shown in Figures 1–3, could function as follows:

Needle guide 102 is attached to medical imaging device 103 via medical imaging device retaining strap 104. The needle guide 102 is readied for receipt of the needle 101 by sliding slidable needle stop 120 to create a gap sufficiently large to accommodate the particular biopsy needle used. The biopsy needle, such as needle 101, is inserted into needle gap 130 and slidable needle stop 120 is released, thereby holding needle 101. The needle 101 is then inserted into the patient. Medical imaging device 103 is used to create a first image of a portion of a human body. The medical imaging device 103 and needle guide 102 are then tilted with respect to the needle 101. This provides a different angle of view of the end 1011 of the needle 101. A second image is then created by the medical imaging device 103. The needle may be held stationary and the medical imaging device 103 and needle guide 102 tilted, or vice versa.

The tilting of the needle 101 or needle guide 102 is done by applying a force between the two. As the angle of separation between the vertical axis 107 and the longitudinal axis of the needle 101 increases, the amount of contact between the needle 101 and planar needle engagement surface 112 and top leading edge 220 increases. This increases the friction on the needle 101, thereby increasing the force needed to move the needle 101 to larger angular separations with respect to the needle guide 102.

Throughout this description, reference is made to a medical imaging system, because it is believed that the beneficial aspects of the present invention would be most readily apparent when used in connection with medical imaging; however, it should be understood that the present invention is not intended to be limited to imaging, and should be hereby construed to include other medical tools, equipment and methodologies as well, where it is desirable to guide a needle.

Throughout this document, references are made to "vertical" and "horizontal". These terms are intended to mean "substantially vertical" and "substantially horizontal". Minor deviations from vertical and minor deviations from horizontal are intended to be included therein. Also see the above definition on vertical axis 107.

It is thought that the method and apparatus of the present invention will be understood from the foregoing description and that it will be apparent that various changes may be made in the form, construct steps, and arrangement of the parts and steps thereof, without departing from the spirit and scope of the invention or sacrificing all of their material advantages. The form herein described is merely a preferred exemplary embodiment thereof.

What is claimed is:

1. An improved needle guide apparatus for use with a medical imaging transceiver assembly, of the type having a predetermined shape, a vertical axis and further of the type which produces an image field, the needle guide apparatus comprising:

a strap which is configured for coupling around a medical imaging transceiver assembly;

said strap being conformable to a predetermined shape;

a biopsy needle guide coupled to and receiving support from said strap;

said biopsy needle guide being coupled with said medical imaging transceiver by said strap, such that said strap and said needle guide, in series, completely encircle a portion of said medical imaging transceiver; and said biopsy needle guide further comprising a structure which is configured to receive therein a biopsy needle and further configured to limit, in at least one dimension, movement of the biopsy needle extending through said biopsy needle guide.

2. A needle guide apparatus of claim 1 wherein said structure is further configured to limit movement of a biopsy needle extending through the biopsy needle guide at a non-parallel and non-perpendicular angle with respect to the vertical axis, so that a lower end of the biopsy needle intersects the image field when the biopsy needle is inserted into a human body below the medical imaging transceiver assembly.

3. A needle guide apparatus of claim 2 wherein said biopsy needle guide has a first needle stop which is substantially fixed with respect to a coupling with said strap; and, a slidable needle stop which is movable with respect to said coupling with said strap; and whereby movement of said slidable needle stop results in a variable needle gap between first needle stop and slidable needle stop, so as to accept therein needles of various gauges.

4. A needle guide apparatus of claim 3 wherein said slidable needle stop is biased toward said first needle stop, so that said needle gap tends to be minimized.

5. A needle guide apparatus of claim 4 wherein said slidable needle stop has a plurality of predetermined positions such that once said slidable needle stop is positioned at a point further from said first needle stop than one of said plurality of predetermined positions, then a biasing force which biases said slidable needle stop toward said first needle stop is insufficient, without an additional external source of force, to move said slidable needle stop past said one of said plurality of predetermined positions.

6. A needle guide apparatus of claim 5 wherein said first needle stop has a planar needle engagement surface; and, said slidable needle stop has a top leading edge which is planar and parallel with respect to said planar needle engagement surface.

7. A needle guide of claim 6 further comprising a bottom angled leading edge which is not parallel with said planar needle engagement surface.

8. A needle guide of claim 7 wherein said bottom angled leading edge is contoured to at least partially circumferentially engage a needle disposed in said needle gap.

9. A needle guide of claim 8 wherein said biasing force increases as said needle gap increases.

10. A needle guide of claim 9 further comprising a plurality of detents formed on an interface between said slidable needle stop and a needle guide main body.

11. A needle guide of claim 10 wherein said plurality of detents have increasing size characteristics as separation from said first needle stop increases.

12. A needle guide of claim 11 wherein said biasing force is provided by a spring.

13. A needle guide apparatus of claim 2 wherein said strap is an elastic band and the at least one dimension is orthogonal to a longitudinal axis of the biopsy needle.

14. A needle guide apparatus of claim 13 wherein said elastic band is an endless elastic band.

15. A needle guide apparatus of claim 1 wherein said biopsy needle guide is indirectly coupled to said strap.

16. A needle guide apparatus of claim 15 wherein said biopsy needle guide is indirectly coupled to said strap by a bracket coupled to said strap.

17. A needle guide comprising:

a first needle stop, having a first needle engagement surface;

a second needle stop having a second needle engagement surface;

a needle receiving gap formed by said first needle receiving surface and said second needle receiving surface;

said needle receiving gap having an open end, such that a needle, having a longitudinal axis, disposed therein can be tilted in tilt direction orthogonal to the longitudinal axis and can be tilted beyond a limit of one of said first needle stop and said second needle stop; so that the needle can be displaced from said needle receiving gap;

said needle receiving gap further configured to guide a biopsy needle by limiting motion of a biopsy needle in a limited direction orthogonal to said longitudinal axis and simultaneously permitting motion of said needle in said tilt direction which is orthogonal to both said limited direction and said longitudinal axis;

said first needle stop and said second needle stop being configured to permit relative movement therebetween, so as to provide adjustment of a gap width of said needle receiving gap; and whereby said needle guide is adjustable to accommodate needles of varying gauges.

18. A needle guide of claim 17 wherein a biasing force is applied to one of said first needle stop and said second needle stop so that said needle tends to remain stationary unless acted upon by a force other than gravity.

19. A method of imaging a biopsy comprising the steps of:

disposing a biopsy needle, having a longitudinal axis, in a needle guide which has an adjustable needle gap width;

the needle guide being coupled to a medical imaging transceiver having a vertical axis;

causing said biopsy needle to enter a human body at a first angle with respect to said vertical axis;

generating a first image of a lower end of said biopsy needle;

applying a force between said biopsy needle and said needle guide to overcome an increasing frictional force which is necessarily increased as an angular separation increases between the vertical axis and the longitudinal axis increases;

said force causing a tilting of said medical imaging transceiver with respect to said biopsy needle; and generating a second image which is different from said first image, at least in part as a result of the tilting of said medical imaging transceiver.

20. An apparatus comprising:

an elastic strap;

a needle guide main body coupled to said elastic strap;

a first needle stop orthogonally fixed to said needle guide main body;

said first needle stop having a planar needle engagement surface;

a slidable needle stop, slidably coupled to said needle guide main body;

said slidable needle stop having a top leading edge which is parallel with and opposing said planar needle engagement surface;

said top leading edge and said planar needle engagement surface forming a needle gap;

said slidable needle stop having a sliding spring stop coupled thereto;

a fixed spring stop coupled to said needle guide main body;

a spring disposed between said sliding spring stop and said fixed spring stop, for providing a biasing force on said slidable needle stop;

said needle guide main body having an interface with said slidable needle stop, where said interface has a plurality of detents at predetermined locations which correspond to conventional biopsy needle gauges; and, said spring providing a needle stabilizing force which maintains a biopsy needle disposed in said needle gap stationary, with respect to said planar needle engagement surface.

* * * * *